United States Patent
Kawarasaki et al.

(10) Patent No.: US 6,881,842 B2
(45) Date of Patent: Apr. 19, 2005

(54) PROCESS FOR PRODUCING TRICYCLIC FUSED HETEROCYCLIC DERIVATIVE

(75) Inventors: Tadao Kawarasaki, Ibaraki (JP); Hideo Hashimoto, Takarazuka (JP); Kiminori Tomimatsu, Minoo (JP)

(73) Assignee: Takeda Chemical Industries, Ltd., Osaka (JP)

( * ) Notice: Subject to any disclaimer, the term of this patent is extended or adjusted under 35 U.S.C. 154(b) by 92 days.

(21) Appl. No.: 10/381,002

(22) PCT Filed: Sep. 20, 2001

(86) PCT No.: PCT/JP01/08165
§ 371 (c)(1),
(2), (4) Date: Mar. 20, 2003

(87) PCT Pub. No.: WO02/24696
PCT Pub. Date: Mar. 28, 2002

(65) Prior Publication Data
US 2003/0191150 A1 Oct. 9, 2003

(30) Foreign Application Priority Data
Sep. 21, 2000 (JP) ......................... 2000-286574

(51) Int. Cl.$^7$ ...................... C07D 401/06; C07D 401/14
(52) U.S. Cl. ............................ 546/94; 546/79; 546/80; 546/93; 546/98
(58) Field of Search ............................ 546/94, 79, 80, 546/93, 98

(56) References Cited

U.S. PATENT DOCUMENTS 5,686,466 A * 11/1997 Goto et al. .................. 514/323

FOREIGN PATENT DOCUMENTS

| EP | 0 607 864 | 7/1994 |
|---|---|---|
| EP | 0 655 451 | 5/1995 |
| EP | 1 118 322 | 7/2001 |
| JP | 7-206854 | 8/1995 |
| WO | 98/40383 | 9/1998 |
| WO | 98/46590 | 10/1998 |
| WO | 00/18391 | 4/2000 |

* cited by examiner

Primary Examiner—Charanjit S. Aulakh
(74) Attorney, Agent, or Firm—Wenderoth, Lind & Ponack, L.L.P.

(57) ABSTRACT

A process for easily and industrially advantageously producing both a tricyclic fused heterocyclic derivative having acetylcholinesterase inhibitory activity and an intermediate for the derivative. The process for producing the target compounds comprises the following reaction.

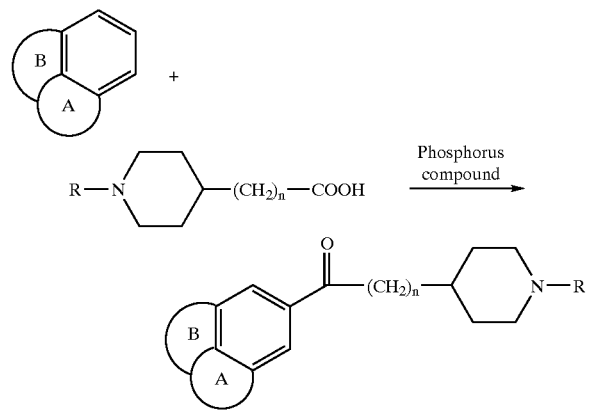

12 Claims, No Drawings

PROCESS FOR PRODUCING TRICYCLIC FUSED HETEROCYCLIC DERIVATIVE

This application is a U.S. national stage of International Application No. PCT/JP 01/08165 filed Sep. 20. 2001.

TECHNICAL FIELD

The present invention relates to a process for producing a tricyclic fused heterocyclic derivative having acetylcholinesterase inhibitory activity which is useful as a medicament and an intermediate thereof.

BACKGROUND TECHNIQUE

Until now, as a process for synthesizing a tricyclic fused heterocyclic derivative having acetylcholinesterase inhibitory activity and an intermediate thereof, Friedel-Crafts reaction of a tricyclic fused heterocyclic ring with an acid chloride in the presence of aluminium chloride in a halogen solvent has been reported (JP 7-206854 A).

OBJECTS OF THE INVENTION

Since in the aforementioned previous process, 1,2-dichloroethane and methylene chloride which are an environmental pollutant and are remarkably restricted in their use are used as a reaction solvent, and many steps are involved, it is desired to develop a process for producing a tricyclic fused heterocyclic derivative and an intermediate thereof, which is inexpensive and simple.

SUMMARY OF THE INVENTION

The present inventors studied various processes for producing a tricyclic fused heterocyclic derivative and, as a result, found for the first time that when a tricyclic fused heterocyclic ring and a piperidinecarboxylic acid derivative are subjected to dehydration-condensation in the presence of a polyphosphoric acid, the piperidinecarboxylic acid derivative is bound to a particular desired position of the tricyclic fused heterocyclic ring, thereby obtaining the desired derivative at a better yield and at the low cost and simply, and that this process is a satisfactory industrial process. Based on these findings, the present inventors intensively studied and completed the present invention.

That is, the present invention relates to:

(1) A process for producing a compound represented by the formula:

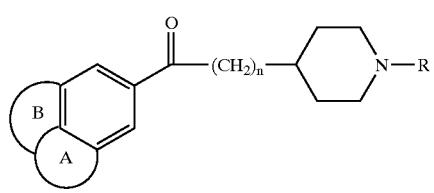

wherein the symbols are as defined hereinafter, or a salt thereof, which comprises:

reacting a compound represented by the formula:

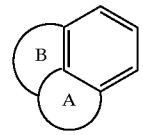

wherein one of the ring A and the ring B is an optionally substituted heterocyclic ring, and the other is an optionally substituted 5- to 8-membered ring which may contain hetero atom(s), or a salt thereof, with a compound represented by the formula:

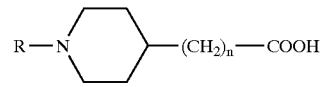

wherein R is a hydrogen atom, an optionally substituted alkyl group or an optionally substituted acyl group, and n is an integer of 1 to 6, or a salt thereof, in the presence of a phosphorus compound;

(2) The process according to the above (1), wherein the phosphorus compound is polyphosphoric acid;

(3) The process according to the above (1), wherein the formula:

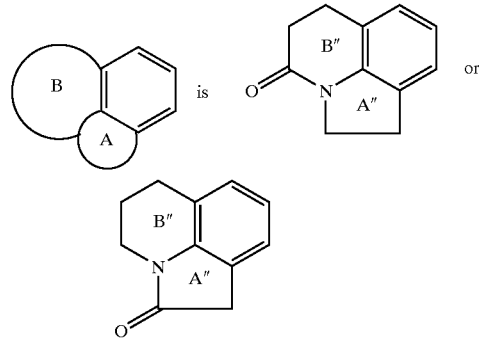

wherein each of the ring A" and the ring B" ring is an optionally substituted nitrogen-containing heterocyclic ring;

(4) The process according to the above (1), wherein R is an optionally substituted acyl group;

(5) The process according to the above (1), wherein R is an acetyl group;

(6) A process for producing 8-[3-(1-acetyl-4-piperidinyl)-1-oxopropyl-1,2,5,6-tetrahydro-4H-pyrrolo[3,2,1-ij]quinoline-4-one, which comprises reacting, 2,5,6-tetrahydro-4H-pyrrolo[3,2,1-ij]quinoline-4-one with 1-acetyl-4-piperidinepropionic acid in the presence of a phosphorus compound;

(7) A process for producing a compound represented by the formula:

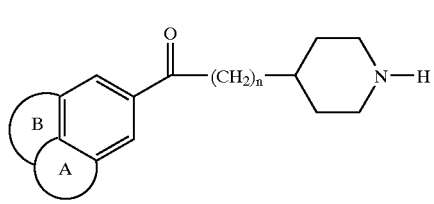

(IV)

wherein the symbols are as defined hereinafter, or a salt thereof, which comprises:

reacting a compound represented by the formula:

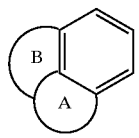

(I)

wherein one of the ring A and the ring B is an optionally substituted heterocyclic ring, and the other is an optionally substituted 5- to 8-memberd ring which may contain hetero atom(s), or a salt thereof, with a compound represented by the formula:

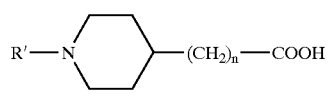

(II')

wherein R' is an optionally substituted acyl group, and n is an integer of 1 to 6, in the presence of a phosphorus compound, and deacylating the resulting compound represented by the formula:

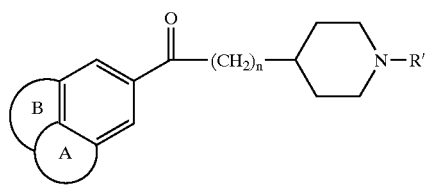

(III')

wherein the symbols are as defined above, or a salt thereof;

(8) The process according to the above (7), wherein deacylation is conducted with about 1 to about 6 N hydrochloric acid;

(9) A process for producing 8-[3-(4-piperidinyl)-1-oxopropyl]-1,2,5,6-tetrahydro-4H-pyrrolo[3,2,1-ij]quinoline-4-one, which comprises reacting 1,2,5,6-tetrahydro-4H-pyrrolo[3,2,1-ij]quinoline-4-one with 1-acetyl-4-piperidinepropionic acid in the presence of a phosphorus compound, and deacetylating the resulting 8-[3-(1-acetyl-4-piperidinyl)-1-oxopropyl-1,2,5,6-tetrahydro-4H-pyrrolo[3,2,1-ij]quinoline-4-one;

(10) A process for producing a compound represented by the formula:

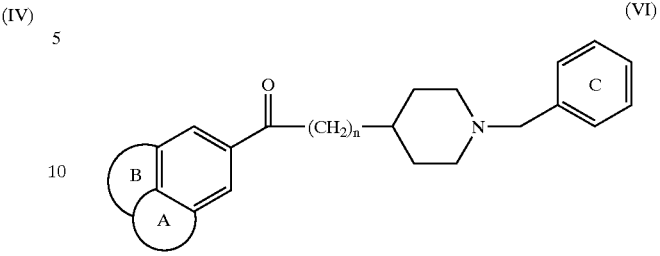

(VI)

wherein the symbols are as defined hereinafter, or a salt thereof, which comprises:

reacting a compound represented by the formula:

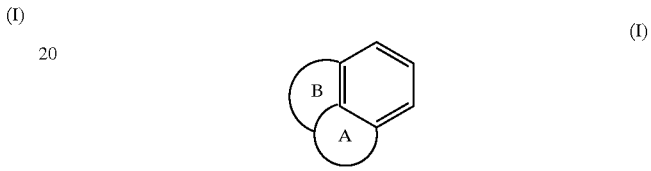

(I)

wherein one of the ring A ring and the ring B is an optionally substituted heterocyclic ring, and the other is an optionally substituted 5- to 8-membered ring which may contain hetero atom(s), or a salt thereof, with a compound represented by the formula:

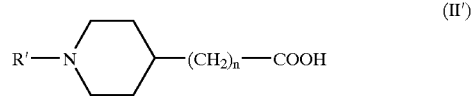

(II')

wherein R' is an optionally substituted acyl group, and n is an integer of 1 to 6, or a salt thereof, in the presence of a phosphorus compound, deacylating the resulting compound represented by the formula:

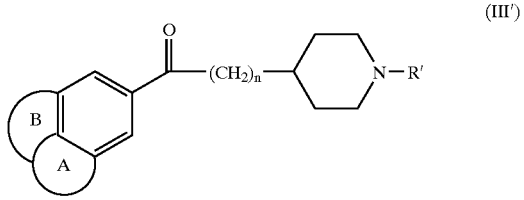

(III')

wherein the symbols are as defined, or a salt thereof, and reacting the resulting compound represented by the formula:

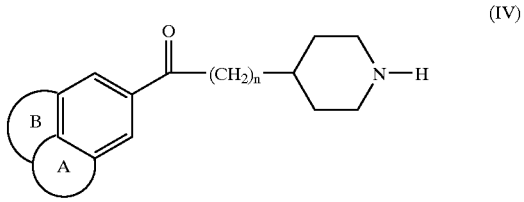

(IV)

wherein the symbols are as defined above, or a salt thereof, with a compound represented by the formula:

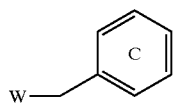

(V)

wherein the ring C is an optionally substituted benzene ring, and W is a leaving group, or a salt thereof;

(11) The process according to the above (10), wherein the ring C is a benzene ring substituted with a halogen;

(12) A process for producing 8-[3-[1-[(3-fluorophenyl)methyl]-4-piperidinyl]-1-oxopropyl]-1,2,5,6-tetrahydro-4H-pyrrolo[3,2,1-ij]quinoline-4-one, which comprises reacting 1,2,5,6-tetrahydro-4H-pyrrolo[3,2,1-ij]quinoline-4-one with 1-acetyl-4-piperidinepropionic acid in the presence of a phosphorus compound, deacetylating the resulting 8-[3-(1-acetyl-4-piperidinyl)-1-oxopropyl-1,2,5,6-tetrahydro-4H-pyrrolo[3,2,1-ij]quinoline-4-one, and reacting the resulting 8-[3-(4-piperidinyl)-1-oxopropyl]-1,2,5,6-tetrahydro-4H-pyrrolo[3,2,1-ij]quinoline-4-one with 3-fluorobenzyl chloride; and the like.

DETAILED EXPLANATION OF THE INVENTION

As the "heterocyclic ring" in the "optionally substituted heterocyclic ring" represented by the ring A or the ring B in the above formulas, for example, a 5- to 9-membered ring containing 1 to 3 hetero atom(s) selected from a nitrogen atom, an oxygen atom and a sulfur atom is used. Specifically, for example, pyridine, pyrazine, pyrimidine, imidazole, furan, thiophene, pyrrolidine, piperidine, hexamethyleneimine, tetrahydrofuran, piperazine, morpholine, thiomorpholine, etc., are used. In particular, a 5- to 9-membered non-aromatic heterocyclic containing one hetero atom or the same or different two hetero atoms (e.g. pyrrolidine, piperidine, hexamethyleneimine, tetrahydrofuran, piperazine, morpholine, thiomorpholine, etc.) is preferable. In particular, for example, a non-aromatic heterocyclic ring containing one hetero atom selected from a nitrogen atom, an oxygen atom and a sulfur atom, and a non-aromatic heterocyclic ring containing one nitrogen atom and one hetero atom selected from a nitrogen atom, an oxygen atom and a sulfur atom are frequently used.

As the "5- to 8-membered ring which may contain hetero atom(s)" represented by the ring A or the ring B, a 5- to 8-membered heterocyclic or carbocyclic ring is used, and the ring may be substituted. The 5- to 8-membered carbocyclic ring may be a benzene ring, or a saturated or unsaturated ring and, for example, benzene, cyclopentane, cyclopentene, cyclohexane, cyclohexene, cyclohexadiene, cycloheptane, cycloheptene, cycloheptadiene, etc., are used. In addition, when the ring A or the ring B has hetero atom(s) in the ring, that is, the ring A or the ring B is a heterocyclic ring, as the hetero atom(s), for example, 1 to 3 atom(s) selected from a nitrogen atom, an oxygen atom and a sulfur atom is (are) used, and the ring A or the ring B may be either aromatic or non-aromatic. As the aromatic heterocyclic ring, pyridine, furan, thiophene, etc., are used. As the non-aromatic heterocyclic ring, a non-aromatic heterocyclic ring exemplified with respect to the ring A or the ring B is preferable.

That is, examples of the compound (I) include 1H,3H-naphtho[1,8-cd][1,2]oxazine, naphtho[1,8-de]-1,3-oxazine, naphtho[1,8-de]-1,2-oxazine, 1,2,2a,3,4,5-hexahydrobenzo[cd]indole, 2,3,3a,4,5,6-hexahydro-1H-benzo[de]quinoline, 4H-pyrrolo[3,2,1-ij]quinoline, 1,2,5,6-tetrahydro-4H-pyrrolo[3,2,1-ij]quinoline, 5,6-dihydro-4H-pyrrolo[3,2,1-ij]quinoline, 1H,5H-benzo[ij]quinolizine, azepino[3,2,1-hi]indole, 1,2,4,5,6,7-hexahydroazepino[3,2,1-hi]indole, 1H-pyrido[3,2,1-jk][1]benzazepine, 5,6,7,8-tetrahydro-1H-pyrido[3,2,1-jk][1]benzazepine, 1,2,5,6,7,8-hexahydro-1H-pyrido[3,2,1-jk][1]benzazepine, 2,3-dihydro-1H-benzo[de]isoquinoline, 1,2,3,4,4a,5,6,7-octahydronaphtho[1,8-bc]azepine, 2,3,5,6,7,8-hexahydro-1H-pyrido[3,2,1-jk][1]benzazepine, and the like.

As the compound (1), for example, a compound represented by the formula:

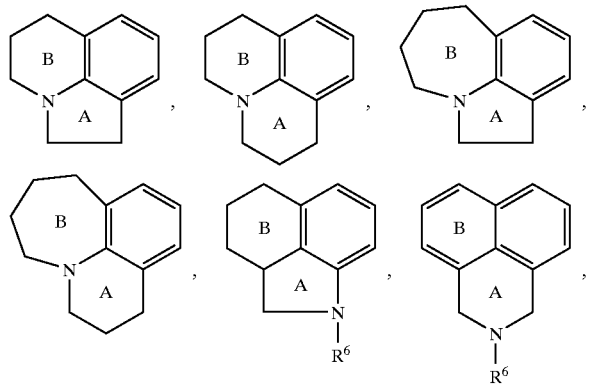

wherein R⁶ is a hydrogen atom, an optionally substituted hydrocarbon group or an optionally substituted acyl group, and the other symbols are as defined above, or a salt thereof is preferable.

As the compound (I), a compound represented by the formula:

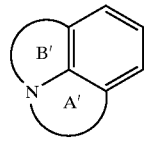

wherein the ring A' is an optionally substituted 5- or 6-membered nitrogen-containing heterocyclic ring, and the ring B' is an optionally substituted 5- to 7-membered nitrogen-containing heterocyclic ring, or a salt thereof, that is, a compound represented by the formula:

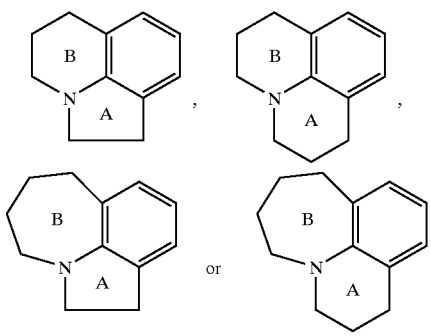

wherein the symbols are as defined above, or a salt thereof is more preferable.

As the compound (I), a compound represented by the formula:

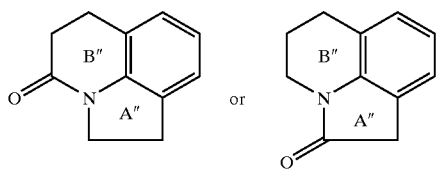

wherein each of the ring A" and the ring B" is an optionally substituted nitrogen-containing heterocyclic ring, or a salt thereof is most preferable.

The ring A and the ring B may be substituted, and the substituent may be present at any arbitrary carbon atom of the ring A and the ring B. As the substituent(s), for example, 1 to 5 substituent(s) selected from a halogen atom (e.g. fluoro, chloro, bromo, iodo, etc.), a nitro group, a cyano group, an oxo group, a hydroxy group, a $C_{1-4}$alkoxy group (e.g. methoxy, ethoxy, propyloxy, butyloxy, isopropyloxy, etc.), a $C_{1-4}$ alkylthio group (e.g. methylthio, ethylthio, propylthio, etc.), an amino group, a mono-or di-$C_{1-4}$ alkylamino group (e.g. methylamino, ethylamino, propylamino, dimethylamino, diethylamino, etc.), a 5- to 7-membered cyclic amino group which may have 1 to 3 hetero atom(s), for example, selected from a nitrogen atom, an oxygen atom and a sulfur atom in addition to carbon atoms and one nitrogen atom (e.g., pyrrolidino, piperidino, morpholino, thiomorpholino, etc.), a $C_{1-4}$ alkyl-carbonylamino group (e.g. acetylamino, propionylamino, butyrylamino, etc.), a $C_{1-4}$ alkylsufonylamino group (e.g. methylsulfonylamino, ethylsulfonylamino, etc.), a $C_{1-4}$ alkoxy-carbonyl group (e.g. methoxycarbonyl, ethoxycarbonyl, propoxycarbonyl, etc.), a carboxyl group, a $C_{1-6}$ alkyl-carbonyl group (e.g. methylcarbonyl, ethylcarbonyl, propylcarbonyl, etc.), a carbamoyl group, a mono- or di-$C_{1-4}$ alkyl-carbamoyl group (e.g. methylcarbamoyl, ethylcarbamoyl, etc.), a $C_{1-6}$ alkylsulfonyl group (e.g. methylsulfonyl, ethylsulfonyl, propylsulfonyl etc.), etc., are used.

Among them, an oxo group, and a $C_{1-6}$ alkyl group such as methyl are preferable and, inter alia, an oxo group is preferable.

When the ring A and the ring B have a nitrogen atom in the ring, those rings may have a substituent on the nitrogen atom. That is, the ring A and the ring B may have

>N—R$^6$ wherein R$^6$ is a hydrogen atom, an optionally substituted hydrocarbon group or an optionally substituted acyl group, in the ring.

As the "optionally substituted hydrocarbon group" represented by R$^6$, for example, a $C_{1-6}$ alkyl group (e.g. methyl, ethyl, n-propyl, isopropyl, etc.) and a $C_{7-10}$ aralkyl group (e.g. phenylmethyl, phenylethyl, etc.), etc., which may be substituted with 1 to 3 substituent(s) selected from a halogen atom (e.g. fluoro, chloro, bromo, iodo, etc.), a nitro group, a $C_{1-4}$ alkoxy group (e.g. methoxy, ethoxy, etc.), a hydroxy group, etc., are preferable. In particular, an unsubstituted benzyl group is frequently used.

As the "optionally substituted acyl group" represented by R$^6$, for example, formyl, $C_{1-6}$ alkyl-carbonyl (e.g. acetyl, propionyl, etc.), benzoyl, $C_{1-6}$ alkylsulfonyl (e.g. methanesulfonyl, ethanesulfonyl, etc.), benzenesulfonyl, $C_{1-6}$ alkoxy-carbonyl (e.g. methoxycarbonyl, ethoxycarbonyl, t-butoxycarbonyl, etc.), benzyloxycarbonyl, etc., which may be substituted with 1 to 3 substituent(s) selected from a halogen atom (e.g. fluoro, chloro, bromo, iodo, etc.), a nitro group, a $C_{1-6}$alkoxy group (e.g. methoxy, ethoxy, etc.), a hydroxy group, an amino group, a mono- or di-$C_{1-6}$ alkylamino group (e.g. methylamino, ethylamino, dimethylamino, diethylamino, etc.), etc., are preferable.

In the aforementioned formulas, examples of a substituent in the ring A', the ring B', the ring A" and the ring B" include the same substituents as those in the ring A and the ring B.

As the substituent of the ring A' and the ring B', an oxo group is preferable, and the ring A" and the ring B" are preferably unsubstituted.

In the aforementioned formulas, examples of the "optionally substituted alkyl group" represented by R include a $C_{1-6}$ alkyl group (e.g. methyl, ethyl, n-propyl, isopropyl, etc.) optionally substituted with 1 to 3 substituent(s) selected from (1) a halogen atom (e.g. fluoro, chloro, bromo, iodo, etc.), (2) nitro group, (3) a $C_{1-6}$alkoxy group (e.g. methoxy ethoxy, etc.), (4) a hydroxy group, (5) a phenyl group optionally substituted with 1 to 3 substituent(s) selected from $C_{1-6}$ alkyl (e.g. methyl, ethyl, etc.), a halogen atom (e.g. fluoro, chloro, bromo, iodo, etc.), nitro, cyano, amino, mono- or di-$C_{1-6}$ alkylamino (e.g. methylamino, ethylamino, dimethylamino, diethylamino, etc.), hydroxy, $C_{1-6}$alkoxy (e.g. methoxy, ethoxy, etc.), phenyl-$C_{1-6}$ alkoxy (e.g. benzyloxy, etc.), $C_{1-4}$ alkylenedioxy (e.g. methylenedioxy, etc.), etc.

Examples of the "optionally substituted acyl group" represented by R and R' include the same "optionally substituted acyl group" as that represented by R$^6$.

As R and R', an optionally substituted acyl group is preferable, and a $C_{1-6}$ alkyl-carbonyl group (e.g. acetyl group) is more preferable.

In the aforementioned formulas, while n is an integer of 1 to 6, 2 or 3 are preferable, and 2 is more preferable.

In the aforementioned formulas, examples of the "optionally substituted benzene ring" represented by the ring C include a benzene ring optionally substituted with 1 to 3 substituent(s) selected from $C_{1-6}$ alkyl (e.g. methyl, ethyl, etc.), halogen atom (e.g. fluoro, chloro, bromo, iodo, etc.), nitro, cyano, amino, mono-or di-$C_{1-6}$alkylamino (e.g. methylamino, ethylamino, dimethylamino, diethylamino, etc.), hydroxy, $C_{1-6}$ alkoxy (e.g. methoxy, ethoxy, etc.), phenyl-$C_{1-4}$ alkoxy (e.g. benzyloxy, etc.) and $C_{1-4}$ alkylenedioxy (e.g. methylenedioxy, etc.).

As the ring C, a benzene ring substituted with a halogen atom such as fluoro, etc., amino, etc., is preferable, and a benzene ring substituted with a halogen atom is more preferable.

Examples of the "leaving group" represented by W in the above formulas include a halogen atom (e.g. chloro, bromo, iodo, etc.), optionally halogenated $C_{1-6}$ alkylsulfonyloxy (e.g. methanesulfonyloxy, ethanesulfonyloxy, trifluoromethanesulfonyloxy, etc.), optionally substituted $C_{6-10}$ arylsulfonyloxy, etc. Examples of the substituent of the "optionally substituted $C_{6-10}$ arylsulfonyloxy" include 1 to 3 substituent(s) selected from a halogen atom, optionally halogenated $C_{1-6}$alkyl and optionally halogenated $C_{1-6}$ halogenated alkoxy. Examples of the "optionally substituted $C_{6-10}$arylsulfonyloxy" include benzenesulfonyloxy, p-toluenesulfonyloxy, 1-naphthalenesulfonyloxy, 2-naphthalenesulfonyloxy, etc.

As W, a halogen atom such as chloro is preferable.

As a salt of the compounds represented by the formulas (I), (II), (II'), (III), (III'), (IV) and (V), for example, salts with inorganic acids (e.g. hydrochloric acid, phosphoric acid, hydrobromic acid, sulfuric acid, nitric acid, etc.), or salts with organic acids (e.g. acetic acid, trifluoroacetic acid, formic acid, propionic acid, fumaric acid, maleic acid, succinic acid, tartaric acid, citric acid, malic acid, oxalic acid, benzoic acid, methanesulfonic acid, benzenesulfonic acid, p-toluenesulfonic acid, etc.) are used. Further, when each compound has an acidic group such as —COOH, the compound may form a salt with inorganic bases (e.g. alkali metal and alkaline earth metal such as sodium, potassium, calcium and magnesium, etc., and ammonia) or organic bases (e.g. triethylamine, triethylamine, pyridine, picoline, ethanolamine, diethanolamine, triethanolamine, dicyclohexylamine, N,N-dibenzylethylenediamine, etc.).

A process for producing the compound (III), (IV) or (VI) which is useful as a tricyclic fused heterocyclic derivative having acetylcholinesterase inhibitory activity and an intermediate thereof will be described below.

In the process of the present invention, a compound (I) and a compound (II) are subjected to dehydration-condensation in the presence of a phosphorus compound to obtain a compound (III).

The amount of the compound (II) to be used is about 1 to 10 moles, preferable about 1 to 2 moles relative to 1 mole of the compound (I).

Examples of the phosphorus compound used in the present invention include 1 or 2 or more selected from polyphosphoric acid, polyphosphoric acid ester, phosphorus pentaoxide, phosphorus pentaoxide-phosphoric acid, phosphorus pentaoxide-methanesulfonic acid, phosphorus oxychloride-zinc (II) chloride, etc. Among them, polyphosphoric acid is preferable.

The amount of the phosphorus compound to be used is about 1 to 100 moles, preferably about 1 to 20 moles relative to 1 mole of the compound (II).

The reaction temperature is usually about 0 to 160° C., preferable about 20 to 120° C. The reaction time is usually about 0.1 to 30 hours, preferably about 1 to 10 hours.

In this reaction, it is preferable that the phosphorus compound is used as it is as a solvent. The reaction may be carried out in the presence of a solvent which is inert to the reaction. As the "inert solvent", aromatic hydrocarbons (e.g. benzene, toluene, xylene, chlorobenzene, etc.), ethers (e.g. diglyme, diethyl ether, diisopropyl ether, t-butyl methyl ether, diphenyl ether, dioxane, 1,2-dimethoxyethane, etc.), aliphatic hydrocarbons (e.g. hexane, pentane, cyclohexane, etc.), amides (e.g. N,N-dimethylformamide, N,N-dimethylacetamide, 1-methyl-2-pyrrolidone, hexamethylphosphorictriamide, etc.), nitrites (e.g. acetonitrile, propionitrile, etc.), and a mixture of 2 or more thereof may be used. Among them, toluene, tetrahydrofuran, N,N-dimethylformamide, etc., are preferable.

When the compound (I) and the compound (II) are commercially available, they may be used as they are, or those compounds may be prepared by a method known per se (JP-A 7-206854) or a similar method.

Next, a compound wherein R is an optionally substituted acyl group in the formula (III), that is, a compound (III') may be further deacylated to obtain a compound (IV).

In this reaction, a deacylating agent such as hydrochloric acid, hydrobromic acid, sulfuric acid and the like is usually used. Among them, hydrochloric acid is preferable, and the concentration of hydrochloric acid is preferably about 1 to 12 N, more preferably about 1 to 6 N.

The amount of the deacylating agent to be used is about 1 to 50 moles, preferably about 2 to 5 moles relative to 1 mole of the compound (IV).

The reaction temperature is usually about 20 to 120° C., preferably about 60 to 100° C. The reaction time is usually about 0.1 to 30 hours, preferably about 1 to 15 hours.

In this reaction, 1 to 12 N hydrochloric acid is used as it is as a solvent in some cases, but the reaction may also be carried out in the presence of a solvent which is inert to the reaction. As the "inert solvent", aromatic hydrocarbons (e.g. benzene, toluene, xylene, chlorobenzene, etc.), ethers (e.g. diglyme, diethyl ether, diisopropyl ether, t-butyl methyl ether, diphenyl ether, dioxane, 1,2-dimethoxyethane, etc.), aliphatic hydrocarbons (e.g. hexane, pentane, cyclohexane, etc.), alcohols (e.g. methanol, ethanol, isopropyl alcohol, 2-butanol, t-butanol, 2-methyl-2-butanol, etc.), and a mixture of 2 or more thereof may be used. Among them, toluene, tetrahydrofuran and ethanol are preferable.

Then, the thus obtained compound (IV) or a compound wherein R is a hydrogen atom in the formula (III) and a compound (V) are reacted in the presence or the absence of a base to obtain a compound (VI).

The amount of the compound (V) to be used is about 1 to 10 moles, preferably about 1 to 3 moles relative to 1 mole of the compound (IV).

Examples of the "base" include hydrides of an alkali metal or an alkaline earth metal (e.g. lithium hydride, sodium hydride, potassium hydride, calcium hydride, etc.), amides of an alkali metal or an alkaline earth metal (e.g. lithium amide, sodium amide, lithium diisopropylamide, lithium dicyclohexylamide, lithium hexamethyldisilazide, sodium hexamethyldisilazide, potassium hexamethyldisilazide, etc.), lower alkoxides of an alkali metal or an alkaline earth metal (e.g. sodium methoxide, sodium ethoxide, potassium tert-butoxide, etc.), carbonates of an alkali metal or an alkaline earth metal (e.g. sodium bicarbonate, sodium carbonate, potassium carbonate, etc.), organic bases (e.g. organic bases such as amines such as triethylamine, diisopropylethylamine, N-methylmorpholine, dimethylaminopyridine, DBU (1,8-diazabicyclo[5.4.0]undec-7-ene), DBN (1,5-diazadicyclo[4.3.0]non-5-ene), etc.; basic heterocyclic compounds such as pyridine, imidazole, and 2,6-lutidine, etc.), etc. Among them, carbonates of an alkali metal or an alkaline earth metal are preferable. The amount of the "base" to be used is about 1 to 10 moles, preferably about 1 to 3 moles relative to 1 mole of the compound (V).

The reaction temperature is usually about −10 to 150° C., preferably about 0 to 80° C. The reaction time is usually about 0.1 to 30 hours, preferably about 1 to 15 hours.

This reaction is carried out in the presence of a solvent which is inert to the reaction. As the "inert solvent", for example, aromatic hydrocarbons (e.g. benzene, toluene, xylene, chlorobenzene, etc.), ethers (e.g. diethyl ether, diisopropyl ether, t-butyl methyl ether, diphenyl ether, tetrahydrofuran, dioxane, 1,2-dimethoxyethane, etc.), aliphatic hydrocarbons (e.g. hexane, pentane, cyclohexane, etc.), amides (e.g. N,N-dimethylformamide, N,N-dimethylacetamide, 1-methyl-2-pyrrolidone, hexamethylphosphorictriamide, etc.), sulfoxides (e.g. dimethyl sulfoxide, etc.), primary alcohols (e.g. methanol, ethanol, etc.), nitrites (e.g. acetonitrile, propionitril, etc.), water and a mixture of 2 or more thereof are used. Among them, N,N-dimethylformamide, ethanol, acetonitrile, etc., are preferable.

This reaction is carried out in the presence of an inorganic salt (e.g. halogenated alkali metal salt such as sodium iodide, sodium bromide, potassium iodide, potassium bromide, etc.) as necessary.

The thus obtained compound (III), (IV) or (VI) can be isolated and purified from a reaction mixture by a separating means known per se (e.g. concentration, concentration under reduced pressure, solvent extraction, precipitation, recrystallization, transferring dissolution, chromatography, etc.).

The desired end compounds [compound (III) (except that R is a hydrogen atom) and compound (VI)] have acetylcholinesterase inhibitory activity. Therefore, these compounds are useful as an agent for preventing or treating senile dementia. Further, they can be used as a bladder excretion modifier. For example, they can be used as an agent for preventing or treating urination disorder caused by the following 1) to 6), in particular, urination difficulty: 1) prostatomegary, 2) bladder cervical obstruction, 3) neurogenic bladder, 4) diabetes, 5) operation and 6) bladder muscle tension reduction. Further, they are also useful as an agent for preventing or treating urination disorder such as pollakiuria, urinal incontinence and the like.

The following Examples illustrate the present invention in more detail but do not limit the present invention.

Abbreviations used in the present text have the following meanings.

s: singlet
d: doublet
t: triplet
m: multiplet
J: coupling constant
Hz: Hertz
CDCl$_3$: heavy chloroform
DMSO-d$_6$: heavy dimethyl sulfoxide
$^1$H-MMR: proton nuclear magnetic resonance $^1$H-NMR spectrum is measured with Brukka DPX 300 (300 MHz) type spectrometer using tetramethylsilane as an internal standard, and the total δ value is shown in ppm.

EXAMPLE 1

Synthesis of 8-[3-(1-acetyl-4-piperidinyl)-1-oxopropyl]-1,2,5,6-tetrahydro-4H-pyrrolo[3,2,1-ij]quinoline-4-one A mixture of 2.5 kg of 1-acetyl-4-piperidinepropionic acid, 2.17 kg (1 equivalent) of 1,2,5,6-tetrahydro-4H-pyrrolo[3,2,1-ij]quinoline-4-one and 26.0 kg of polyphosphoric acid was stirred at about 105° C. for 8 hours under nitrogen and 13 L of cold water at about 5° C. was slowly added dropwise thereto while maintaining about 70° C. Further, 25 L of a mixture of toluene-acetonitrile (1:1) was added at about 55° C. and pH was adjusted to about 8.5 by adding 25% aqueous ammonia solution (about 50 L) while maintaining about 55° C. The layers were separated, 10 L of a mixture of toluene-acetonitrile (1:1) was added to the aqueous layer, and the layers were separated. The organic layers were combined and concentrated to a volume of the solution of about 10 L. To the residue was added 9 L of isopropyl ether at about 20° C. to precipitate crystals. The mixture was stirred at about 20° C. for about 1.5 hours and then at about 5° C. for about 1.5 hours. Precipitated crystals were separated, washed with about 6 L of a mixture of isopropyl ether-ethyl acetate (1:1) cooled to about 5° C., and 10 L of isopropyl ether cooled to about 5° C., and dried to obtain 3.78 kg (yield 85%) of the desired compound as crystals.

Elementary Analysis

Calcd: C: 71.16, H: 7.39, N: 7.90, 0: 13.54
Found: C: 71.20, H: 7.36, N: 7.80
$^1$H-NMR(CDCl$_3$): 1.13–1.19 (2H, m), 1.64–1.79 (5H, m), 2.09 (3H, s), 2.53 (1H, t), 2.72 (2H, t, J=9.7 Hz), 2.93–3.05 (5H, m), 3.23 (2H, t, J=8.4 Hz), 3.80 (1H, d), 4.14 (2H, t, J=8.4 Hz), 5.61 (1H, d), 7.67 (1H, s), 7.72 (1H, s)

EXAMPLE 2

Synthesis of 8-[3-(4-piperidinyl)-1-oxopropyl]-1,2,5,6-tetrahydro-4H-pyrrolo[3,2,1-ij]quinoline-4-one A mixture of 3.95 kg of 8-[3-(1-acetyl-4-piperidinyl)-1-oxopropyl]-1,2,5,6-tetrahydro-4H-pyrrolo[3,2,1-ij]quinoline-4-one and 19.8 L of 2 N HCl was stirred at about 85° C. for about 10 hours. After cooled to about 35° C., 12 L of toluene was added to the reaction mixture, the layers were separated, and pH was adjusted to about 13 by adding 30% NaOH (about 10 L) to the aqueous layer while maintaining about 30° C. Further, 20 L of a mixture of toluene-acetonitrile (1:1) was added thereto, and the layers were separated. To the aqueous layer was added 12 L of a mixture of toluene-acetonitrile (1:1), and the layers were separated. The organic layers were combined, 12 L of 30% brine was added thereto, and the layers were separated. To the organic layer were added 346 g of active carbon and 346 g of silica gel, followed by stirring for about 15 minutes. The insolubles were filtered off, and washed with 6 L of a mixture of toluene-acetonitrile (1:1). The filtrate was concentrated to a volume of the solution of about 7 L. To the residue was added 3 L of toluene, and the mixture was stirred at about 40° C. Under nitrogen, 666 g of acetic acid was added at about 30° C. over about 15 minutes. The mixture was stirred at about 25° C. for 1.5 hours and then at about 5° C. for 1 hour. Precipitated crystals were separated, and washed with 28 L of a mixture of toluene-acetonitrile (1:1) cooled to about 5° C. The wet crystals were suspended in 65 L of a mixture of toluene-acetonitrile (1:1), 30% NaOH was added (about 10 L) thereto, pH was adjusted to 13.5, and the layers were separated. To the aqueous layer was added 8 L of a mixture of toluene-acetonitrile (1:1), and the layers were separated. The organic layers were combined, and washed with 12 L of 30% brine. The organic layer was washed again with 12 L of 30% brine. To the organic layer were added 346 g of active carbon and 346 g of silica gel, the mixture was stirred for about 15 minutes. The insolubles were filtered off, and washed with 6 L of a mixture of toluene-acetonitrile (1:1). The same procedures were repeated twice. The organic layer was concentrated, and 5 L of water was added to the residue, followed by re-concentration. The same procedures were repeated twice. Under nitrogen, 5 L of water was added to the residue, and 5 L of 30% brine was added at about 20° C. over about 15 minutes. Seed crystals were added, and the mixture was stirred at about 20° C. for 1.5 hours and then at about 5° C. for 1 hour. The desired compound was separated under nitrogen, washed with 4 L of 30% brine cooled to about 5° C., and dried to give 1.78 kg (yield 51%) of the desired compound as crystals.

Elementary Analysis
Calcd: C: 73.05, H: 7.74, N: 8.97, O: 10.24
Found: C: 72.90, H: 7.65, N: 9.06
$^1$H-NMR(CDCl$_3$): 1.12–1.22 (2H, m), 1.40–1.50 (1H, m), 1.64–1.74 (4H, m), 2.59 (2H, td, J=12, 2.4 Hz), 2.72 (2H, t, J=7.5 Hz), 2.93 (2H, t, J=7.5 Hz), 3.00–3.10 (4H, m), 3.23 (2H, t, J=8.4 Hz), 4.13 (2H, t, J=8.4 Hz), 7.67 (1H, s), 7.72 (1H, s)

EXAMPLE 3

Synthesis of 8-[3-[1-[(3-fluorophenyl)methyl]-4-piperidinyl]-1-oxopropyl]-1,2,5,6-tetrahydro-4H-pyrrolo[3,2,1-ij]quinoline-4-one A mixture of 600 g of 8-[3-(4-piperidinyl)-1-oxopropyl]-1,2,5,6-tetrahydro-4H-pyrrolo[3,2,1-ij]quinoline-4-one, 6 L of acetonitrile, 0.3 L of water, 345 g (1.3 equivalent) of potassium carbonate and 278 g (1 equivalent) of 3-fluorobenzyl chloride was stirred at about 55° C. and 12 L of water was added dropwise thereto over about 20 minutes while maintaining about 45° C. The mixture was stirred at about 55° C. for 1.5 hours, and at about 20° C. for 3 hours. Precipitated crystals were separated, and washed with 15 L of water. The wet crystals were suspended in 8.0 L of 10% hydrous methanol-denatured ethanol. The material was dissolved at about 70° C., and passed through a dust-removing filter. The filtrate was stirred at about 20° C. for 1.5 hours, 6.9 L of water was added thereto, and the mixture was stirred at about 20° C. for 3 hours. Crystals were separated, washed with 1.8 L of 50% hydrous methanol-denatured ethanol twice and dried to obtain 0.71 kg (yield 88%) of the desired compound as crystals.
m.p.: 114° C.

Elementary Analysis Calcd: C: 74.26, H: 6.95, N: 6.66, F: 4.52, O: 7.61 Found: C: 74.27, H: 6.97, N: 6.53, F: 4.52
$^1$H-NMR(DMSO-d$_6$): 1.16 (2H, qd, J=11.9, 3.5 Hz), 1.21–1.30 (1H, m), 1.53 (2H, m), 1.64–1.67 (2H, d, J=11.9 Hz), 1.89 (2H, t, J=11.9 Hz), 2.59 (2H, t, J=7.8 Hz), 2.77 (2H, d, J=11.9 Hz), 2.94 (2H, t, J=7.6 Hz), 2.97 (2H, J=7.8 Hz), 3.17 (2H, t, 8.5 Hz), 3.44 (2H, s), 3.98 (2H, t, J=8.5 Hz), 7.05 (1H, m), 7.10 (1H, d), 7.12 (1H, d, J=7.9 Hz), 7.35 (1H, td, J=7.9, 6.1Hz), 7.72 (1H, m), 7.73 (1H, m) IR(KBr, vcm$^{-1}$): 2020, 1660, 1597, 1491, 1387, 1336, 1128, 802
UVmax(CH$_3$CN): 310 nm

EXAMPLE 4

Synthesis of 8-[3-(1-acetyl-4-piperidinyl)-1-oxopropyl]-1,2,5,6-tetrahydro-4H-pyrrolo[3,2,1-ij]quinoline-4-one A mixture of 1-acetyl-4-piperidinepropionic acid (1.99 g, 9.99 mmol), 1,2,5,6-tetrahydro-4H-pyrrolo[3,2,1-ij]quinoline-4-one (1.73 g, 9.99 mmol) and polyphosphoric acid (24 g) was stirred at about 105° C. for 7 hours under nitrogen. Cold water (16 mL) at about 5° C. was slowly added dropwise thereto at −40 to 70° C. and 25% aqueous ammonia was added dropwise thereto at 40 to 50° C. to adjust pH to 8.5. A mixture of toluene-acetonitrile (1:1) (20 mL) was added. The layers were separated, a mixture of toluene-acetonitrile (1:1) (10 mL) was added to the aqueous layer, and the layers were separated. The organic layers were combined, and concentrated to a volume of the solution of ⅕. Diisoporpyl ether (7 mL) was added to the residue to precipitate crystals. The mixture was stirred at about 25° C. for about 1 hour and then at 0 to 5° C. for about 1 hour. Precipitated crystals were separated, washed with diisopropyl ether (3 mL) and dried to obtain 3.47 g (yield 98.6%) of the desired compound as crystals.

EXAMPLE 5

Synthesis of 8-[3-(4-piperidinyl)-1-oxopropyl]-1,2,5,6-tetrahydro-4H-pyrrolo[3,2,1-ij]quinoline-4-one 8-[3-(1-acetyl-4-piperidinyl)-1-oxopropyl]-1,2,5,6-tetrahydro-4H-pyrrolo[3,2,1-ij]quinoline-4-one (10 g, 28.2 mmol) and 2 N hydrochloric acid (50 mL) were stirred at about 90° C. for 8 hours. After cooled to about 25° C., toluene (30 mL) was added to the reaction mixture, the layers were separated, and 30% aqueous sodium hydroxide solution (16 mL) was added to the aqueous layer to adjust pH to 13.8. A mixture of toluene-acetonitrile (1:1) (50 mL) was added thereto, and the layers were separated. A mixture of toluene-acetonitrile (1:1) (50 mL) was added to aqueous layer, and the layers were separated. The organic layers were combined, 30% brine (30 mL) was added, and the layers were separated. The organic layer was concentrated under reduced pressure to obtain 8.55 g (yield 92.5%) of the desired compound as a solid.

EXAMPLE 6

Synthesis of 8-[3-[1-[(3-fluorophenyl)methyl]-4-piperidinyl]-1-oxopropyl]-1,2,5,6-tetrahydro-4H-pyrrolo[3,2,1-ij]quinoline-4-one A mixture of 8-[3-(4-piperidinyl)-1-oxopropyl]-1,2,5,6-tetrahydro-4H-pyrrolo[3,2,1-ij]quinoline-4-one (4 g, 12.8 mmol), acetonitrile (26 mL), water (1.4 mL), potassium carbonate (2.3 g, 16.6 mmol) and 3-fluorobenzyl chloride (1.55 mL, 12.8 mmol) was stirred at about 50 to 55° C. After cooling, water (84 mL) was added dropwise thereto. The mixture was stirred at room temperature for about 1 hour. Precipitated crystals were separated, washed with water (80 mL) and dried to obtain 5.09 g (yield 95%) of the desired compound as crystals.

Industrial Applicability

According to the process of the present invention, a tricyclic fused heterocyclic derivative having acetylcholinesterase inhibitory activity which is useful as a medicament, and an intermediate thereof can be prepared at a better yield, effectively and at an industrial large scale by an inexpensive and simple process.

What is claimed is:
1. A process for producing a compound represented by the formula:

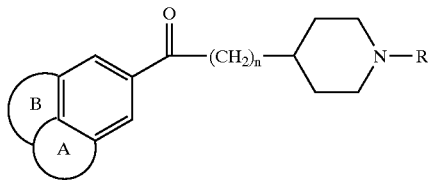

wherein the symbols are as defined hereinafter, or a salt thereof, which comprises:
reacting a compound represented by the formula:

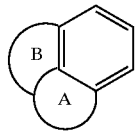

wherein one of the ring A and the ring B is a 5- to 9-membered aromatic or non-aromatic heterocyclic ring containing 1 to 3 hetero atom(s) selected from a nitrogen atom, an oxygen atom and a sulfur atom, which may be substituted with 1 to 5 substituent(s) selected from a halogen atom, a nitro group. a cyano group, an oxo group, a hydroxy group, a C$_{1-6}$ alkyl group, a C$_{1-4}$ alkoxy group, a C$_{1-4}$ alkylthio group, an amino group, a mono-or di-$C_{1-4}$ alkylamino group, a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-4}$ alkoxy-carbonyl group, a carboxyl group, a $C_{1-4}$ alkylcarbonyl group, a carbamoyl group, a mono- or di-$C_{1-4}$ alkyl-carbamoyl group, and a $C_{1-6}$ alkylsulfonyl group, and the other is a 5- to 8-membered aromatic or non-aromatic heterocyclic ring containing 1 to 3 atom(s) selected from a nitrogen atom, an oxygen atom and a sulfur atom or a 5- to 8-membered saturated or unsaturated carbocyclic ring, which may be substituted with 1 to 5 substituent(s) selected from a halogen atom, a nitro group, a cyano group, an oxo group, a hydroxy group, a $C_{1-6}$ alkyl group, a $C_{1-4}$ alkoxy group, a $C_{1-4}$ alkylthio group, an amino group, a mono-or di-$C_{1-4}$ alkylamino group, a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group, and a $C_{1-6}$ alkylsulfonyl group, or a salt thereof, with a compound represented by the formula:

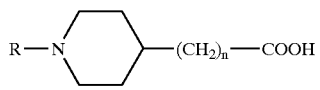

wherein R is a hydrogen atom, an optionally substituted alkyl group or an optionally substituted acyl group, and n is an integer of 1 to 6, or a salt thereof, in the presence of a phosphorus compound.

2. The process according to claim 1, wherein the phosphorus compound is a polyphosphoric acid.

3. The process according to claim 1, wherein the formula:

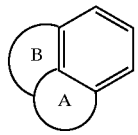 is

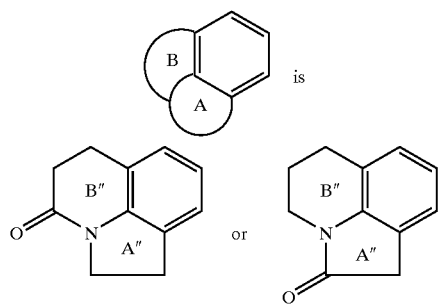

wherein each of the ring A" and the ring B" ring is an optionally substituted nitrogen-containing heterocyclic ring.

4. The process according to claim 1, wherein R is an optionally substituted acyl group.

5. The process according to claim 1, wherein R is an acetyl group.

6. A process for producing 8-[3-(1-acetyl-4-piperidinyl)-1-oxopropyl-1,2,5,6-tetrahydro-4H-pyrrolo[3,2,1-ij]quinoline-4-one, which comprises reacting 1,2,5,6-tetrahydro-4H-pyrrolo[3,2,1-ij]quinoline-4-one with 1-acetyl-4-piperidinepropionic acid in the presence of a phosphorus compound.

7. A process for producing a compound represented by the formula:

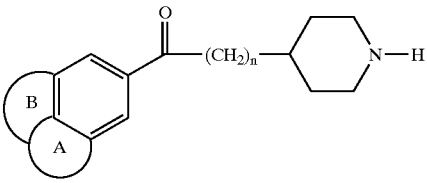

wherein the symbols are as defined hereinafter, or a salt thereof, which comprises:

reacting a compound represented by the formula:

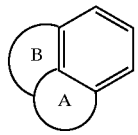

wherein one of the ring A and the ring B is a 5- to 9-membered aromatic or non-aromatic heterocyclic ring containing 1 to 3 hetero atom(s) selected from a nitrogen atom, an oxygen atom and a sulfur atom, which may be substituted with 1 to 5 substituent(s) selected from a halogen atom, a nitro group, a cyano group, an oxo group, a hydroxy group, a $C_{1-6}$ alkyl group, a $C_{1-4}$ alkoxy group, a $C_{1-4}$ alkylthio group, an amino group, a mono- or di-$C_{1-4}$ alkylamino group, a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-4}$ alkoxy-carbonyl group, a carboxyl group, a $C_{1-6}$ alkylcarbonyl group, a carbamoyl group, a mono- or di-$C_{1-4}$ alkyl-carbamoyl group, and a $C_{1-6}$ alkylsulfonyl group, and the other is a 5- to 8-membered aromatic or non-aromatic heterocyclic ring containing 1 to 3 atom(s) selected from a nitrogen atom, an oxygen atom and a sulfur atom or a 5- to 8-membered saturated or unsaturated carbocyclic ring, which may be substituted with 1 to 5 substituent(s) selected from a halogen atom, a nitro group, a cyano group, an oxo group, a hydroxy group, a $C_{1-6}$ alkyl group, a $C_{1-4}$ alkoxy group, a $C_{1-4}$ alkylthio group, an amino group, a mono-or di-$C_{1-4}$ alkylamino group, a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-6}$ alkoxy-carbonyl group, a carboxyl group, a $C_{1-4}$ alkyl-carbonyl group, a carbamoyl group, a mono- or di-$C_{1-4}$ alkyl-carbamoyl group, and a $C_{1-6}$ alkylsulfonyl group, or a salt thereof, with a compound represented by the formula:

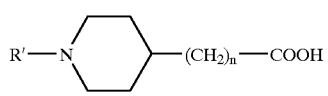

wherein R' is an optionally substituted acyl group, and n is an integer of 1 to 6, in the presence of a phosphorus compound, and deacylating the resulting compound represented by the formula:

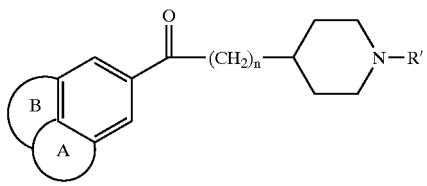

wherein the symbols are as defined above, or a salt thereof.

8. The process according to claim 7, wherein deacylation is conducted with about 1 to about 6 N hydrochloric acid.

9. A process for producing 8-[3-(4-piperidinyl)-1-oxopropyl]-1,2,5,6-tetrahydro-4H-pyrrolo [3,2,1-ij] quinoline-4-one, which comprises reacting 1,2,5,6-tetrahydro-4H-pyrrolo[3,2,1-ij]quinoline-4-one with 1-acetyl-4-piperidinepropionic acid in the presence of a phosphorus compound, and deacetylating the resulting 8-[3-(1-acetyl-4-piperidinyl)-1-oxopropyl-1,2,5,6-tetrahydro-4H-pyrrolo [3,2,1-ij]quinoline-4-one.

10. A process for producing a compound represented by the formula:

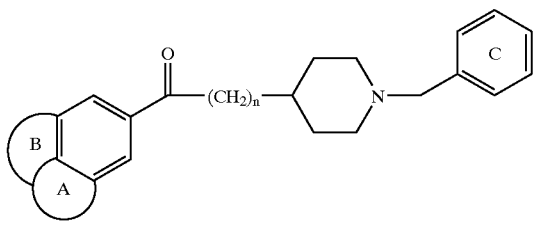

wherein the symbols are as defined hereinafter, or a salt thereof, which comprises:

reacting a compound represented by the formula:

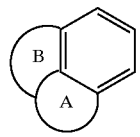

wherein one of the ring A ring and the ring B is a 5- to 9-membered aromatic or non-aromatic heterocyclic ring containing 1 to 3 hetero atom(s) selected from a nitrogen atom, an oxygen atom and a sulfur atom, which may be substituted with 1 to 5 substituent(s) selected from a halogen atom, a nitro group, a cyano group, an oxo group, a hydroxy group, a $C_{1-6}$ alkyl group, a $C_{1-4}$ alkoxy group, a $C_{1-4}$ alkylthio group, an amino group, a mono-or di-$C_{1-4}$ alkylamino group, a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-4}$ alkoxy-carbonyl group, a carboxyl group, a $C_{1-6}$ alkylcarbonyl group, a carbamoyl group, a mono- or di-$C_{1-4}$ alkyl-carbamoyl group, and a $C_{1-6}$ alkylsulfonyl group, and the other is a 5- to 8-membered aromatic or non-aromatic heterocyclic ring containing 1 to 3 atom(s) selected from a nitrogen atom, an oxygen atom and a sulfur atom or a 5- to 8-membered saturated or unsaturated carbocyclic ring, which may be substituted with 1 to 5 substituent(s) selected from a halogen atom, a nitro group, a cyano group, an oxo group, a hydroxy group, a $C_{1-6}$ alkyl group, a $C_{1-4}$ alkoxy group, a $C_{1-4}$ alkylthio group, an amino group, a mono-or di-$C_{1-4}$ alkylamino group. a 5- to 7-membered cyclic amino group which may have 1 to 3 hetero atom(s) selected from a nitrogen atom, an oxygen atom and a sulfur atom in addition to carbon atoms and one nitrogen atom, a $C_{1-4}$ alkylcarbonylamino group, a $C_{1-4}$ alkylsulfonylamino group, a $C_{1-4}$ alkoxy-carbonyl group, a carboxyl group, a $C_{1-6}$ alkyl-carbonyl group, a carbamoyl group, a mono- or di-$C_{1-4}$ alkyl-carbamoyl group, and a $C_{1-6}$ alkylsulfonyl group, or a salt thereof, with a compound represented by the formula:

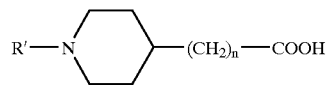

wherein R' is an optionally substituted acyl group, and n is an integer of 1 to 6, or a salt thereof, in the presence of a phosphorus compound, deacylating the resulting compound represented by the formula:

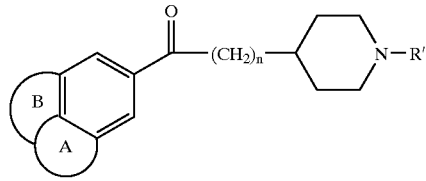

wherein the symbols are as defined, or a salt thereof, and reacting the resulting compound represented by the formula:

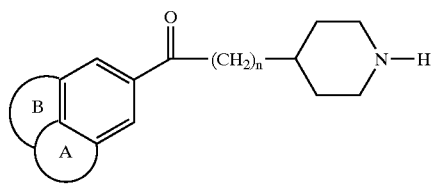

wherein the symbols are as defined above, or a salt thereof, with a compound represented by the formula:

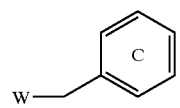

wherein the ring C is an optionally substituted benzene ring, and W is a leaving group, or a salt thereof.

11. The process according to claim 10, wherein the ring C is a benzene ring substituted with a halogen.

12. A process for producing 8-[3-[1-[(3-fluorophenyl)methyl]-4-piperidinyl]-1-oxopropyl]-1,2,5,6-tetrahydro-4H-pyrrolo [3,2,1-ij]quinoline-4-one, which comprises reacting 1,2,5,6-tetrahydro-4H-pyrrolo[3,2,1-ij]quinoline-4-one with 1-acetyl-4-piperidinepropionic acid in the presence of a phosphorus compound, deacetylating the resulting 8-[3-(1-acetyl-4-piperidinyl)-1-oxopropyl-1,2,5,6-tetrahydro-4H-pyrrolo [3,2,1-ij]quinoline-4-one, and reacting the resulting 8-[3-(4-piperidinyl)-1-oxopropyl]-1,2,5,6-tetrahydro-4H-pyrrolo [3,2,1-ij]quinoline-4-one with 3-fluorobenzyl chloride.

* * * * *